US008492353B2

(12) United States Patent
Wakamatsu et al.

(10) Patent No.: US 8,492,353 B2
(45) Date of Patent: Jul. 23, 2013

(54) ANTIAGING COMPOSITION

(75) Inventors: Kosaburo Wakamatsu, Kyoto (JP); Fumiki Harano, Kyoto (JP); Takashige Koba, Fukuoka (JP); Shigeo Shinohara, Kyoto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1452 days.

(21) Appl. No.: 10/523,605

(22) PCT Filed: Aug. 1, 2003

(86) PCT No.: PCT/JP03/09783

§ 371 (c)(1), (2), (4) Date: Feb. 4, 2005

(87) PCT Pub. No.: WO2004/016238

PCT Pub. Date: Feb. 26, 2004

(65) Prior Publication Data

US 2005/0250710 A1 Nov. 10, 2005

(30) Foreign Application Priority Data

Aug. 6, 2002 (JP) ................................ 2002-228368

(51) Int. Cl.
*A61K 31/70* (2006.01)
*A61K 31/34* (2006.01)
*A61K 8/02* (2006.01)

(52) U.S. Cl.
USPC ................ 514/27; 514/47; 514/474; 424/401

(58) Field of Classification Search
USPC .............................. 424/401; 514/27, 47, 474
See application file for complete search history.

(56) References Cited

U.S. PATENT DOCUMENTS

| | | | | |
|---|---|---|---|---|
| 5,605,694 | A | 2/1997 | Nadaud et al. | |
| 5,607,921 | A | 3/1997 | Bernard | |
| 6,180,133 | B1 * | 1/2001 | Quan et al. | 424/448 |
| 6,946,436 | B2 * | 9/2005 | Wakamatsu et al. | 510/417 |
| 2002/0042380 | A1 * | 4/2002 | Castiel et al. | 514/24 |

FOREIGN PATENT DOCUMENTS

| | | | |
|---|---|---|---|
| EP | 0 685 229 | A1 | 12/1995 |
| JP | 47-26687 | B | 7/1972 |
| JP | 59-134706 | A | 8/1984 |
| JP | 09-295915 | A | 11/1997 |
| JP | 10-158149 | A | 6/1998 |
| WO | WO 99/51197 | | 10/1999 |
| WO | WO 99/55302 | | 11/1999 |
| WO | WO 0241853 | A1 * | 5/2002 |
| WO | WO 2005/046574 | A | 5/2005 |

OTHER PUBLICATIONS www.rakuten.co.jp/placen-lab—Mar. 29, 2002.
www.nuinternational.co.jp/seibun.html+AMP—Jun. 6, 2003.

* cited by examiner

*Primary Examiner* — Sreeni Padmanabhan
*Assistant Examiner* — Jody Karol
(74) *Attorney, Agent, or Firm* — Finnegan, Henderson, Farabow, Garrett & Dunner, L.L.P.

(57) ABSTRACT

The present invention provides an antiaging composition capable of efficiently retarding skin aging skin aging, particularly, alleviating skin pigmentation. The present invention also provides a method for potentiating the antiaging action of ascorbic acids. The invention provides an antiaging composition containing at least one member selected from the group consisting of ascorbic acid, a derivative of ascorbic acid, and a salt thereof (A), and a purine nucleic acid-related substance (B). The invention provides a method for potentiating the antiaging action of such component (A) by the combined use of at least one member selected from the group consisting of ascorbic acid, a derivative of ascorbic acid, and a salt thereof (A), with a purine nucleic acid-related substance (B).

10 Claims, 1 Drawing Sheet

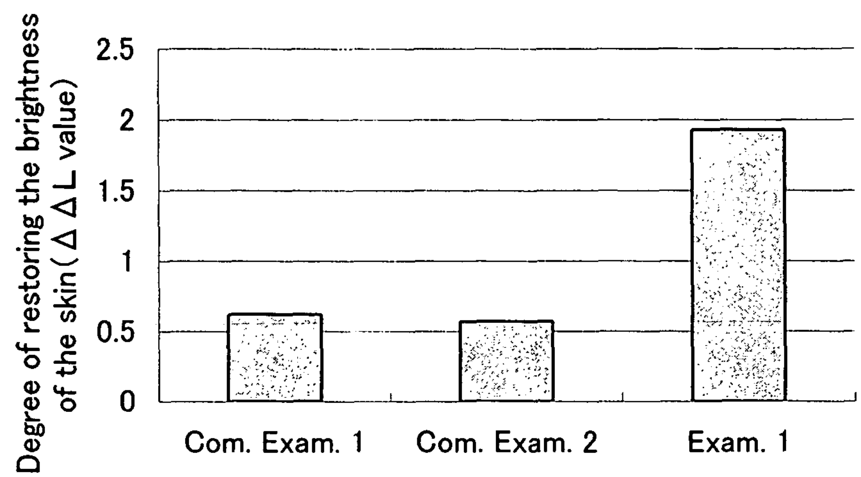
Degree of restoring the brightness of the skin (ΔΔL value)
2.5
2
1.5
1
0.5
0
Com. Exam. 1
Com. Exam. 2
Exam. 1

ANTIAGING COMPOSITION

This is a national stage application of PCT/JP03/09738, filed on Aug. 1, 2003, which claims priority to Japanese Application 2002-228368, filed on Aug. 6, 2002.

BACKGROUND OF THE INVENTION

Various symptoms of skin aging are caused by aging, sunlight (ultraviolet radiation) exposure, eating habits, stresses, etc. Retarding skin aging is an important health and aesthetic objective. In particular, among the symptoms of skin aging, melasma and freckles can be serious aesthetic concerns for women. The developmental mechanism of melasma and freckles in the skin has not been fully elucidated yet. In general, however, it is considered that melasma and freckles are caused by the deposition of melanin pigments in the epidermis, which are produced in skin cells due to stimuli such as ultraviolet radiation, etc.

Conventionally, external cosmetic preparations comprising substances which have efficacy as a whitening agent such as ascorbic acid and its derivatives, glutathione, kojic acid, arbutin, cysteine, etc. are used for the decrease and treatment of pigmentation such as melasma and freckles. However, such agents for external application are slow in ameliorating pigmentation and their effects are not satisfactory.

Considering such drawbacks of the prior art, the development of means for retarding skin aging, particularly means for efficiently ameliorating pigmentation, has been desired.

SUMMARY OF THE INVENTION

The present invention relates to an antiaging composition. More specifically, the present invention relates to an antiaging composition for retarding skin aging, particularly for efficiently alleviating skin pigmentation.

The present invention also relates to a method for potentiating the antiaging action of ascorbic acid, a derivative of ascorbic acid, or a salt thereof.

Further, the present invention relates to a method for retarding skin aging.

The antiaging composition of the present invention exhibits an excellent skin antiaging effect, particularly a pigmentation preventing effect, since the antiaging action, particularly the pigmentation alleviating action, of ascorbic acids, is synergistically potentiated by a purine nucleic acid-related substance.

Both the ascorbic acids and purine nucleic acid-related substance as components constituting the antiaging composition of the present invention are highly safe to the living body, and they can stably exist even in the presence of other components, such as amino acids, proteins, lipids, saccharides, etc. Therefore, the antiaging composition of the present invention has high safety, and the appearance and properties thereof do not deteriorate, and thus it can be formulated into various externally-applied preparations, such as cosmetics, externally-applied medical or quasi-medical drugs, etc. Therefore, the antiaging composition of the present invention can provide a wide variety of means for retarding skin aging, and in particular, efficiently ameliorating pigmentation.

According to the method for potentiating the antiaging action of ascorbic acids of the present invention, the antiaging action of ascorbic acids can be potentiated by a purine nucleic acid-related substance. Thus, the method of the invention enables the preparation of a composition that exhibits excellent antiaging effects with only a small amount of ascorbic acids.

The method for retarding skin aging of the present invention is useful for maintaining the health and beauty of the skin since skin aging can be efficiently retarded, and in particular, skin pigmentation can be efficiently alleviated.

BRIEF DESCRIPTION OF THE DRAWINGS

FIG. 1 shows the degree of restoring the brightness of the skin (ΔΔL value) obtained in Test Example 1; test solutions of Example 1 (a solution containing 2% (w/w) of ascorbic acid 2-glucoside and 2% (w/w) of AMP), Comparative Example 1 (a solution containing 2% (w/w) of ascorbic acid 2-glucoside and no AMP), and Comparative Example 2 (a solution containing 2% (w/w) of AMP and no ascorbic acid 2-glucoside) were applied to skin pigmentation sites of colored guinea pigs twice per day for 35 days, respectively.

DETAILED DESCRIPTION OF THE INVENTION

An object of the present invention is to solve the above-described problems of the prior art. More specifically, an object of the present invention is to provide an antiaging composition capable of effectively retarding skin aging, and alleviating skin pigmentation in particular. Another object of the invention is to provide a method for potentiating the antiaging action of ascorbic acid, a derivative of ascorbic acid, and a salt thereof. Still another object of the present invention is to provide a method for retarding skin aging by effectively potentiating the antiaging action of ascorbic acid, a derivative of ascorbic acid, and a salt thereof (hereinafter these compounds are sometimes referred to as "ascorbic acids" collectively).

The present inventors carried out intensive research and found out that the combined use of at least one member selected from the group consisting of ascorbic acid, a derivative of ascorbic acid, and a salt thereof, with a purine nucleic acid-related substance synergistically potentiates the pigmentation-reducing effect of ascorbic acids, and thus skin aging can be retarded, and in particular skin pigmentation can be more efficiently alleviated. The invention has been accomplished based on these findings.

More specifically, the present invention relates to the following antiaging compositions.

Item 1. An antiaging composition comprising the following components (A) and (B):

(A) at least one member selected from the group consisting of ascorbic acid, a derivative of ascorbic acid, and a salt thereof; and (B) a purine nucleic acid-related substance.

Item 2. The antiaging composition according to Item 1, wherein the component (A) is ascorbic acid-2-glucoside, ascorbyl tetraisopalmitate, L-ascorbyl phosphate, or a salt thereof.

Item 3. The antiaging composition according to Item 1, wherein the component (A) is ascorbic acid 2-glucoside or a salt thereof.

Item 4. The antiaging composition according to any one of Items 1 to 3, wherein the component (B) is adenosine 2'-monophosphate, adenosine 3'-monophosphate, adenosine 5'-monophosphate, cyclic adenosine 3',5'-monophosphate, or a salt thereof.

Item 5. The antiaging composition according to any one of Items 1 to 3, wherein the component (B) is adenosine 5'-monophosphate or a salt thereof.

Item 6. The antiaging composition according to Item 1, wherein the component (A) is ascorbic acid 2-glucoside or a salt thereof and the component (B) is adenosine 5'-monophosphate or a salt thereof.

Item 7. The antiaging composition according to any one of Items 1 to 6, wherein the component (A) is contained in a proportion of 0.05 to 10% (w/w) based on the total amount of the antiaging composition.

Item 8. The antiaging composition according to any one of Items 1 to 7, wherein the component (B) is contained in a proportion of 0.05 to 10% (w/w) based on the total amount of the antiaging composition.

Item 9. The antiaging composition according to any one of Items 1 to 8, wherein the component (B) is contained in a proportion of 0.5 to 1000 parts by weight per 100 parts by weight of the component (A).

Item 10. The antiaging composition according to any one of Items 1 to 9, which has a pH in the range of 5 to 7.

Item 11. The antiaging composition according to any one of Items 1 to 10, wherein the composition is a cosmetic, or an externally-applied medical or quasi-medical drug.

Item 12. The antiaging composition according to any one of Items 1 to 11, wherein the composition is used as a composition for alleviating pigmentation.

The invention also relates to the following methods for potentiating the antiaging action of ascorbic acid, a derivative of ascorbic acid, or a salt thereof.

Item 13. A method for potentiating an antiaging action of ascorbic acid, a derivative of ascorbic acid, or a salt thereof, the method comprising using at least one member selected from the group (A) consisting of ascorbic acid, a derivative of ascorbic acid, and a salt thereof, in combination with a purine nucleic acid-related substance (B).

Item 14. The potentiating method according to Item 13, wherein the component (A) is ascorbic acid 2-glucoside, ascorbyl tetraisopalmitate, L-ascorbyl phosphate, or a salt thereof.

Item 15. The potentiating method according to Item 13, wherein the component (A) is ascorbic acid 2-glucoside or a salt thereof.

Item 16. The potentiating method according to any one of Items 13 to 15, wherein the component (B) is adenosine 2'-monophosphate, adenosine 3'-monophosphate, adenosine 5'-monophosphate, cyclic adenosine 3',5'-monophosphate, or a salt thereof.

Item 17. The potentiating method according to any one of Items 13 to 15, wherein the component (B) is adenosine 5'-monophosphate or a salt thereof.

Item 18. The potentiating method according to Item 13, wherein the component (A) is ascorbic acid 2-glucoside or a salt thereof, and the component (B) is adenosine 5'-monophosphate or a salt thereof.

Item 19. The potentiating method according to any one of Items 13 to 18, wherein the component (B) is used, in combination with the component (A), in a proportion of 0.5 to 1000 parts by weight per 100 parts by weight of the component (A).

Item 20. The potentiating method according to any one of Items 13 to 19, the method comprising incorporating the component (B) into a composition containing the component (A).

Item 21. The potentiating method according to Item 20, wherein the composition contains the component (A) in a proportion of 0.05 to 10% (w/w) based on the total amount of the composition.

Item 22. The potentiating method according to Item 20 or 21, wherein the composition is an externally-applied composition for the skin.

Item 23. The potentiating method according to any one of Items 13 to 22 for potentiating a pigmentation-alleviating action of ascorbic acid, a derivative of ascorbic acid, or a salt thereof.

The present invention further relates to the following methods for retarding skin aging.

Item 24. A method for retarding skin aging comprising applying to the skin at least one member selected from the group (A) consisting of ascorbic acid, a derivative of ascorbic acid, and a salt thereof, and a purine nucleic acid-related substance (B).

Item 25. The method for retarding skin aging according to Item 24, wherein the component (A) is ascorbic acid 2-glucoside, ascorbyl tetraisopalmitate, L-ascorbyl phosphate, or a salt thereof.

Item 26. The method for retarding skin aging according to Item 24, wherein the component (A) is ascorbic acid 2-glucoside or a salt thereof.

Item 27. The method for retarding skin aging according to any one of Items 24 to 26, wherein the component (B) is adenosine 2'-monophosphate, adenosine 3'-monophosphate, adenosine 5'-monophosphate, cyclic adenosine 3',5'-monophosphate, or a salt thereof.

Item 28. The method for retarding skin aging according to any one of Items 24 to 26, wherein the component (B) is adenosine 5'-monophosphate or a salt thereof.

Item 29. The method for retarding skin aging according to Item 24, wherein the component (A) is ascorbic acid 2-glucoside or a salt thereof and the component (B) is adenosine 5'-monophosphate or a salt thereof.

Item 30. The method for retarding skin aging according to any one of Items 24 to 29, the method comprising using the component (B) in a proportion of 0.5 to 1000 parts by weight per 100 parts by weight of the component (A).

Item 31. The method for retarding skin aging according to any one of Items 24 to 30, the method comprising applying to the skin a composition containing the components (A) and (B).

Item 32. The method for retarding skin aging according to any one of Items 24 to 31, the method comprising applying to the skin an antiaging composition according to any one of Items 1 to 12.

Item 33. The method for retarding skin aging according to any one of Items 24 to 32, the method being carried out for alleviating pigmentation.

The invention relates to the following modes of embodiments.

Item 34. Use of at least one member selected from the group consisting of ascorbic acid, a derivative of ascorbic acid, and a salt thereof, and a purine nucleic acid-related substance for the manufacture of an antiaging composition.

Item 35. Use of a purine nucleic acid-related substance for potentiating an antiaging action of ascorbic acid, a derivative of ascorbic acid, or a salt thereof.

Item 36. Use of at least one member selected from the group consisting of ascorbic acid, a derivative of ascorbic acid, and a salt thereof, and a purine nucleic acid-related substance for antiaging.

BEST MODE

The term "antiaging" used in connection with the invention means retarding skin aging, particularly alleviating skin pigmentation. The phrase "alleviating (ameliorating) skin pigmentation" used herein means reducing or alleviating (ameliorating) excessive deposition of pigment in skin tissues.

(1) Antiaging Composition

The antiaging composition of the present invention contains at least one member selected from the group consisting of ascorbic acid, a derivative of ascorbic acid, and a salt thereof (hereinafter referred to as "component (A)"), in combination with a purine nucleic acid-related substance (hereinafter referred to as "component (B)").

The antiaging composition of the present invention contains at least one member selected from the group consisting of ascorbic acid, a derivative of ascorbic acid, and a salt thereof, as the component (A).

Any of water soluble and lipid soluble ascorbic acid derivatives can be used in the invention. More specifically, examples of ascorbic acid derivatives usable as the component (A) include ascorbyl 2,6-dipalmitate, ascorbyl 6-stearate, ascorbyl-2-sulfate, ascorbyl-2-phosphate, ascorbic acid 2-glucoside, ascorbic acid glucosamine, L-dehydroascorbic acid, ascorbyl 6-palm itate, L-ascorbyl tetraisopalmitate, ascorbyl tetraisopalmitate, L-ascorbyl phosphate, etc. Preferable among them are ascorbic acid 2-glucoside, ascorbyl tetraisopalmitate and L-ascorbyl phosphate, with ascorbic acid 2-glucoside being particularly preferable.

Processes for producing the above-mentioned ascorbic acid derivatives are not limited. For example, they may be produced by a biochemical process or by organic synthesis. In view of safety and cost efficiency, those produced by a biochemical process are preferable. Examples of methods for producing an ascorbic acid derivative, for example ascorbic acid 2-glucoside, using a biochemical process include a method which comprises adding a glycosyltransferase singly, or a combination of a glycosyltransferase and glucoamylase, to a solution of L-ascorbic acid and an α-glucoside.

Any salt of ascorbic acid and any derivative thereof can be used as the component (A) without limitation. Specific examples of salts of ascorbic acid and derivatives thereof include salts of alkali metals, such as sodium, potassium, etc.; salts of alkaline earth metals, such as calcium, magnesium, barium, etc.; salts of basic amino acids, such as arginine, lysine, etc.; ammonium salts, such as ammonium salts, tricyclohexylammonium salts, etc.; alkanolamine salts, such as monoisopropanolamine salts, diisopropanolamine salts, triisopropanolamine salts, etc.

Preferable examples of the component (A) are ascorbic acid 2-glucoside, ascorbyl tetraisopalmitate, L-ascorbyl phosphate, and a salt thereof. Among these compounds, ascorbic acid 2-glucoside and salts thereof are particularly preferable as the component (A) since the effect of the present invention is remarkably exhibited by using them.

The antiaging composition of the present invention may include one member selected from ascorbic acid, a derivative of ascorbic acid, and a salt thereof as the component (A), or may include two or more members selected therefrom.

The proportion of the component (A) to be incorporated into the antiaging composition of the present invention may be suitably determined without limitation according to the form of the composition, the kind of the component (A) to be employed, the intended effect, etc. For example, the proportion of the total amount of the component (A) is 0.05 to 10% (w/w), preferably 0.5 to 10% (w/w), and more preferably 1 to 10% (w/w), based on the total amount of the antiaging composition.

The antiaging composition of the present invention contains a purine nucleic acid-related substance as the component (B).

Purine nucleic acid-related substances usable in the invention are purine per se or various purine derivatives having a purine nucleus as a skeleton (hereinafter these substances are sometimes referred to as "purine bases" collectively), and salts thereof.

Purine nucleic acid-related substance to be used in the invention are not limited. Examples of purine nucleic acid-related substances include adenine, guanine, hypoxanthine, xanthine, adenosine, guanosine, inosine, adenosine phosphates [(adenosine 2'-monophosphate, adenosine 3'-monophosphate, adenosine 5'-monophosphate (AMP), cyclic adenosine 3',5'-monophosphate (cAMP), adenosine 5'-diphosphate (ADP), adenosine 5'-triphosphate (ATP)], guanosine phosphates (guanosine 3'-monophosphate, guanosine 5'-monophosphate, guanosine 5'-diphosphate, guanosine 5'-triphosphate), adenylosuccinic acid, xanthic acid, inosinic acid, flavine adenine dinucleotide (FAD), nicotinamide adenine dinucleotide (NAD) and the like. Preferable among these are adenosine monophosphates (adenosine 2'-monophosphate, adenosine 3'-monophosphate, AMP, and cAMP). Among these, AMP is particularly preferable as the component (B) since the effect of the present invention can be remarkably demonstrated.

There is no limitation to purine base salts usable in the invention. Specific examples of purine base salts include salts of alkali metals, such as sodium, potassium, etc.; salts of alkaline earth metals, such as calcium, magnesium, barium, etc.; salts of basic amino acids, such as arginine, lysine, etc.; ammonium salts, such as ammonium salts, tricyclohexylammonium salts, etc.; alkanolamine salts, such as monoisopropanolamine salts, diisopropanolamine salts, triisopropanolamine salts, etc. Among the above, alkali metal salts are preferable.

Preferable examples of the component (B) to be employed are monosodium adenosine monophosphate, disodium adenosine monophosphate, or a salt thereof.

The antiaging composition of the present invention may include one member selected from the above-mentioned purine nucleic acid-related substances as the component (B), or may include two or more members freely selected therefrom. When two or more of the above-mentioned purine nucleic acid-related substances are combined to be used as the component (B), various combinations thereof can be used insofar as the effect of the invention is not adversely affected.

The proportion of the component (B) to be employed into the antiaging composition of the present invention may be suitably determined without limitation according to the form of the composition, the intended effect, etc. For example, the proportion of the total amount of the component (B) is in a proportion of 0.5 to 1000 parts by weight, preferably 5 to 500 parts by weight, and more preferably 50 to 500 parts by weight, per 100 parts by weight of the component (A). The proportion of the total amount of the component (B) is 0.05 to 10% (w/w), preferably 0.1 to 7% (w/w), and more preferably 0.5 to 6% (w/w), based on the total amount of the antiaging composition.

Various combinations of the components (A) and (B) can be used without limitation in the antiaging composition of the invention insofar as the composition contains such a combination. Among the antiaging compositions of the invention, those in which the component (A) is ascorbic acid 2-glucoside or a salt thereof and the component (B) is AMP or a salt thereof are preferable. The effect of the invention will be highly enhanced by antiaging compositions comprising such specific combination of components.

The antiaging composition of the invention usually has a pH in the range of weakly acid to neutral. With a view to minimizing irritation to the skin and alleviating pigmentation, the composition preferably has a pH in the range of 5 to 7, more preferably 5.5 to 7. pH adjustors may be incorporated into the externally-applied preparations for the skin so as to control the pH of the antiaging composition of the present invention within the above range. Such pH adjustors are not limited insofar as they are weakly alkaline or alkaline and pharmacologically or cosmetically acceptable. Examples of pH adjusters include sodium hydroxide, L-arginine, aminomethylpropanediol, diisopropanolamine, triethanolamine, etc.

In addition to the above components, the antiaging composition of the invention may contain, as required, a wide variety of components or additives that are generally incorporated into externally-applied preparations. Specific examples include surfactants, solubilizers, fats or oils, polyhydric alcohols, thickeners, antiseptics, bactericides, humectants, colorants, dispersants, antioxidants, sequestering agents, astringents, whiteners, pigments, deodorizers, flavors, etc. Such components may be used singly or in any combination of two or more members.

The antiaging composition of the present invention may take any form without limitation insofar as it is formulated as an externally-applied composition for the skin such as a cosmetic, an externally-applied medical or quasi-medical drug, etc. More specifically, the antiaging composition of the invention may be produced as externally-applicable preparations in desirable forms such as pastes, mousses, gels, liquids, emulsions, suspensions, creams, ointments, sheets, aerosol formulations, spray formulations, liniments, etc., when the above-mentioned components are formulated, as required, into the antiaging composition of the invention, and further other solvents or conventionally-used bases or carriers for externally-applied preparations are added thereinto as required. Such compositions can be produced in a known manner in this field.

The antiaging composition of the present invention is not limited as to modes of use. For example, the antiaging composition of the present invention can be prepared as various externally-applied preparations, such as externally-applied medical drugs; externally-applied quasi-medical drugs; makeup cosmetics such as foundations, rouges, mascaras, eye shadows, eyeliners, face powders, etc; basic skin care products such as emulsions, creams, lotions, oils and packs; washes such as facial washes, cleansing creams and body washes; cleaning agents; cleaners; bath agents, etc.

The antiaging composition of the present invention is used by applying it to the skin as an externally-applied antiaging agent. There is no limitation to the frequency and amount of the antiaging composition of the invention applied to the skin. For example, it may be applied in an appropriate amount to the skin, particularly to pigmentation sites, once or several times per day according to the type and concentration of active ingredients, age of the user, gender, condition of the affected part of the skin, the application form, the intended effect, etc.

The antiaging composition of the present invention can effectively alleviate skin pigmentation, which is one of the symptoms of skin aging, as shown in Examples described later. Accordingly, the antiaging composition of the present invention can also be used as a composition for alleviating pigmentation, or as a whitening composition.

The antiaging composition of the present invention demonstrates, when applied to the skin, excellent skin antiaging effects, particularly, the effect of alleviating pigments and a whitening effect. Accordingly, the present invention provides the use of at least one member selected from the group consisting of ascorbic acid, a derivative of ascorbic acid, and a salt thereof, in combination with a purine nucleic acid-related substance for the production of the antiaging composition; the use of at least one member selected from the group consisting of ascorbic acid, a derivative of ascorbic acid, and a salt thereof, in combination with a purine nucleic acid-related substance for the manufacture of a composition for alleviating pigmentation; and the use of at least one member selected from the group consisting of ascorbic acid, a derivative of ascorbic acid, and a salt thereof, in combination with a purine nucleic acid-related substance for the manufacture of a whitening composition.

(II) Method for Potentiating the Antiaging Action of Ascorbic Acids

The present invention provides the method for potentiating the antiaging action of ascorbic acid, a derivative of ascorbic acid, or a salt thereof. The method is carried out by the combined use of at least one member selected from the group consisting of ascorbic acid, a derivative of ascorbic acid, and a salt thereof (hereinafter these compounds are referred to as "component (A)" collectively), with a purine nucleic acid-related substance (hereinafter referred to as the component (B)).

Ascorbic acid, a derivative of ascorbic acid, and a salt thereof to be used as the component (A), and a purine nucleic acid-related substance to be used as the component (B) for the method of the invention are the same as those usable in the above-described antiaging composition. Various combinations of the components (A) and (B) can be used in the method of the invention.

In the method of the invention, the combination of ascorbic acid 2-glucoside or a salt thereof as the component (A) and AMP or a salt thereof as the component (B) is preferable since the effect of the invention is remarkably demonstrated by the combination.

Although the ratio between the components (A) and (B) in the method of the invention is not limited, the total amount of the component (B) may be 0.5 to 1000 parts by weight, preferably 5 to 500 parts by weight, more preferably 50 to 500 parts by weight, per 100 parts by weight of the total amount of the component (A).

The method of the invention is carried out by, for example, incorporating the component (B) into a composition that contains the component (A) and demonstrates an antiaging effect in such a manner that the proportion of the component (B) may be within the above range. The above manner of carrying out the method of the invention allows production of a composition in which the antiaging action of ascorbic acid, a derivative of ascorbic acid, or a salt thereof is potentiated. Insofar as a composition contains the component (A), the component (B) is incorporated into any kind of composition in the above-described manner of carrying out the method of the invention. For example, compositions in which the total amount of the component (A) is 0.05 to 10% (w/w), preferably 0.5 to 10% (w/w), more preferably 1 to 10% (w/w), based on the total amount of the composition can be mentioned. Preferably, such compositions are externally applied.

The method of the invention can potentiate the effect of alleviating skin pigmentation in particular, among the antiaging effects of ascorbic acids, as shown in Examples described later. Therefore, the method for potentiating the antiaging action of ascorbic acids of the present invention can also be carried out as a method for potentiating the pigmentation alleviating action of ascorbic acids or as a method for potentiating the whitening action of ascorbic acids.

As described above, the antiaging action of ascorbic acids, particularly the pigmentation alleviating action and whitening action, can be potentiated by the combined use of at least one member selected from the group consisting of ascorbic acid, a derivative of ascorbic acid, and a salt thereof, with a purine nucleic acid-related substance. Therefore, the present invention provides the use of a purine nucleic acid-related substance for potentiating the antiaging action of ascorbic acids; the use of a purine nucleic acid-related substance for potentiating the pigmentation alleviating action of ascorbic acids; and the use of a purine nucleic acid-related substance for potentiating the whitening action of ascorbic acids.

(III) Method for Retarding Skin Aging

The present invention provides a method for retarding skin aging. The method is carried out by applying to the skin at least one member selected from the group consisting of ascorbic acid, a derivative of ascorbic acid, and a salt thereof (hereinafter these compounds are referred to as "component (A)" collectively), in combination with a purine nucleic acid-related substance (hereinafter referred to as "components (B)").

Ascorbic acid, a derivative of ascorbic acid, and a salt thereof as the component (A), and a purine nucleic acid-related substance as the component (B) in the method of the invention are the same as those usable in the above antiaging composition. There is no limitation to the modes of combination of the components (A) and (B) in the method of the invention.

In the method of the invention, the effect of the invention is remarkably demonstrated by the combination of ascorbic acid 2-glucoside or a salt thereof as the component (A) and AMP or a salt thereof as the component (B), and thus it is preferable.

Although the ratio between the components (A) and (B) is not limited in the method of the invention, the total amount of the component (B) may be 0.5 to 1000 parts by weight, preferably 5 to 500 parts by weight, and more preferably 50 to 500 parts by weight, per 100 parts by weight of the total amount of the component (A).

In the method of the invention, there is no limitation to the manner of applying the component (A) in combination with the component (B), insofar as these both components can co-exist on the skin. For example, a composition containing the components (A) and (B) may be applied to the skin, or the component (A) singly or a composition containing the same, and the component (B) singly or a composition containing the same, may be successively applied to the skin in any desired order. The above-mentioned both components may be applied to the skin by, for example, spreading or spraying.

Applicable skin for the method of the present invention is not limited, insofar as it is a portion for which antiaging is intended, and preferably a portion in which pigmentation is to be alleviated or prevented.

The method of the present invention is preferably carried out by applying or spraying onto the skin or the like a composition containing the components (A) and (B). The antiaging composition described in (I) above are preferable as a composition containing the components (A) and (B).

There is no limitation to the frequency and amount of the both kinds of the components (A) and (B) applied to the skin. For example, they may be applied in an appropriate amount to the skin once or several times per day according to the age of the user, gender, intended effect, condition of the affected part of the skin, etc. More specifically, when the method of the invention is carried out by using the antiaging composition described in (I) above, a single dose amount can be suitably adjusted such that the amount of the composition applied to the skin or the like is within the range of 0.5 to 10 mg/cm$^2$.

As shown in the Examples below, the effect of ameliorating skin pigmentation is especially remarkable among the antiaging effects demonstrated by the method of the present invention. Therefore, the antiaging method of the present invention can also be carried out as a method for ameliorating pigmentation.

As described above, skin aging can be retarded, and in particular, pigmentation can be alleviated, by applying to the skin at least one member selected from the group consisting of ascorbic acid, a derivative of ascorbic acid, and a salt thereof, in combination with a purine nucleic acid-related substance. Accordingly, the present invention further provides the use of at least one member selected from the group consisting of ascorbic acid, a derivative of ascorbic acid, and a salt thereof, in combination with a purine nucleic acid-related substance for antiaging, and the use of at least one member selected from the group consisting of ascorbic acid, a derivative of ascorbic acid, and a salt thereof, in combination with a purine nucleic acid-related substance for retarding pigmentation.

EXAMPLES

The present invention is described in further detail with reference to Test Examples and Comparative Examples. The scope of the invention is not limited to these Examples, however. In the following Test Examples and Comparative Examples, percentages are all by weight unless otherwise specified.

Test Example 1

Experiment for Evaluating the Pigmentation-Alleviating Effect

The effect of the combined use of ascorbic acid 2-glucoside and adenosine monophosphate for alleviating skin pigmentation was evaluated by a test according to the following method.

1. Preparation of a Test Solution

Ascorbic acid 2-glucoside and AMP were added to a 20% aqueous solution of isopropanol in such a manner that the ratio therebetween is as shown in Table 1, giving various test solutions (Example 1, Comparative examples 1 and 2, and a blank solution; see Table 1).

TABLE 1

| Components | Test solutions | | | |
|---|---|---|---|---|
| | Ex. 1 | Com. Ex. 1 | Com. Ex. 2 | Blank solution |
| Ascorbic acid 2-glucoside | 2% | 2% | 0% | 0% |
| AMP | 2% | 0% | 2% | 0% |

Ascorbic acid 2-glucoside and AMP were added to a 20% aqueous solution of isopropanol in such a manner that the ratio therebetween is as shown in Table 1, yielding various test solutions (Example 1, Comparative examples 1 and 2, and a blank solution; see Table 1).

2. Production of an Animal Model Having Pigmentation

The hair on the back of eight colored guinea pigs (purchased from "KIWA LABORATORY ANIMALS CO., LTD.") was shaved, the shaved back of each guinea pig was exposed to ultraviolet irradiation several times, and four pigmentation sites per animal were produced.

Eleven days after the final ultraviolet irradiation exposure to the guinea pigs, application of the above-described four test solutions to the pigmentation site was initiated. The above-described four test solutions were applied as follows. A suitable amount of one of each test solution (Example 1, reference solutions 1 and 2, and a blank solution) was applied to one of each of the four pigmentation sites of each colored guinea pig. The application of the test solutions was conducted twice per day and continued for 35 days. The test was conducted using eight colored guinea pigs.

The skin brightness (L value) of the pigmentation sites to which each test solution was applied was determined with a colorimeter before application of the test solutions and 35 days after the application. The mean value of the skin brightness of the pigmentation sites to which each test solution was applied was calculated, and the degree of restoring the brightness of the skin of the pigmentation sites to which the test solution of Example 1 and reference solutions 1 and 2 (ΔΔvalue) was calculated according to calculating formula 1.

Degree of restoring the brightness of the skin (ΔΔ*L* value)={(the mean of *L* values 35 days after application of the solution)−(the mean of *L* values before application of the solution)}−{(the mean of *L* values 35 days after application of the blank solution)−(the mean of *L* values before application of the blank solution)}. Calculating formula 1

Results

The obtained results are shown in FIG. 1. FIG. 1 shows the degree of restoring the brightness of the skin (ΔΔL value) when each test solution of Example 1 and reference solutions 1 and 2 was applied to the pigmentation sites of the colored guinea pigs. As can be seen from FIG. 1, it can be seen clarified that the degree of restoring the brightness of the skin of the pigmentation sites to which the test solution of Example 1 was applied is conspicuously higher than that of the sites to which the test solutions of Comparative Tests 1 and 2 were applied. The degree of restoring the brightness of the skin of the pigmentation sites to which the test solution of Example 1 were applied was 1.93, and in contrast thereto the total degree of restoring the brightness of the skin of the pigmentation sites to which the test solutions of Comparative Examples 1 and 2 were applied was 1.19. It was thus confirmed from these results that the combined use of ascorbic acid 2-glucoside and AMP synergistically potentiates the effect of alleviating pigmentation.

The above result shows that the composition containing ascorbic acid 2-glucoside and AMP efficiently alleviates skin pigmentation, and is thus useful for retarding skin aging.

Example 2

Lotion

| | |
|---|---|
| Adenosine 5'-monophosphate | 2.0 (% (w/w)) |
| Ascorbic acid 2-glucoside | 2.0 |
| 1,3-butyleneglycol | 2.0 |
| Concentrated glycerin | 2.0 |
| Polyoxyethylene sorbitan monolaurate (20E.O.) | 1.0 |
| Ethanol | 5.0 |
| Antiseptic | Suitable quantity |
| pH adjuster | Adjusted to pH 6.5 |
| Purified water | Balance |
| Total | 100.0% (w/w) |

Example 3

Cream

| | |
|---|---|
| Adenosine 5'-monophosphate | 2.0 (% (w/w)) |
| Ascorbic acid 2-glucoside | 2.0 |
| Polyoxyalkylene alkyl denatured silicone | 2.0 |
| Decamethylcyclopentasiloxane | 18.0 |
| Liquid paraffin | 4.0 |
| Concentrated glycerin | 3.0 |
| 1,3-butyleneglycol | 4.0 |
| Ethanol | 5.0 |
| Antiseptic | Suitable quantity |
| pH adjuster | Adjusted to pH 6.5 |
| Purified water | Balance |
| Total | 100.0% (w/w) |

Example 4

Emulsion

| | |
|---|---|
| Disodium adenosine 5'-monophosphate | 0.5 (% (w/w)) |
| Ascorbyl tetraisopalmitate | 1.0 |
| Decaglyceryl monostearate | 2.0 |
| Glyceryl monostearate | 1.0 |
| Stearic acid | 3.0 |
| Behenylalcohol | 2.0 |
| Glyceryl tri-2-ethylhexanoate | 5.0 |
| Squalane | 2.0 |
| Decamethylcyclopentasiloxane | 1.0 |
| Hydrogenated soybean phospholipid | 0.3 |
| DL-α-tocopherol acetate | 0.1 |
| Concentrated glycerin | 2.0 |
| 1,3-butyleneglycol | 3.0 |
| Carboxy vinylpolymer | 0.1 |
| Antiseptic | Suitable quantity |
| pH adjuster | Adjusted to pH 6.5 |
| Purified water | Balance |
| Total | 100.0% (w/w) |

Example 5

Essence

| | |
|---|---|
| Disodium adenosine 5'-monophosphate | 1.5 (% (w/w)) |
| Magnesium L-ascorbyl phosphate | 3.0 |
| Dipropyleneglycol | 3.0 |
| Concentrated glycerin | 2.0 |
| Sodium hyaluronate | 0.1 |
| Polyoxyethylene methylpolysiloxane copolymer | 0.2 |
| Methoxyethylene anhydride maleic acid copolymer | 0.2 |
| Ethanol | 3.0 |
| Antiseptic | Suitable quantity |
| pH adjuster | Adjusted to pH 6.5 |
| Purified water | Balance |
| Total | 100.0% (w/w) |

We claim:

1. A method for potentiating a skin pigmentation alleviating action of a composition containing (A) ascorbic acid 2-glucoside, the method comprising the step of incorporating at least one purine nucleic acid-related substance selected from the group (B) consisting of adenosine 2'-monophosphate, adenosine 3'-monophosphate, adenosine 5'-monophosphate, and salts thereof into said composition, wherein component (B) is present in a proportion of 5 to 500 parts by weight per 100 parts by weight of component (A).

2. A potentiating method according to claim 1, wherein the component (B) is adenosine 5'-monophosphate or a salt thereof.

3. A method for alleviating skin pigmentation comprising the step of applying to pigmented skin (A) ascorbic acid 2-glucoside and at least one purine nucleic acid-related substance selected from the group (B) consisting of adenosine 2'-monophosphate, adenosine 3'-monophosphate, adenosine 5'-monophosphate, and salts thereof, wherein component B is present in a proportion of 5 to 500 parts by weight per 100 parts by weight of component (A).

4. A potentiating method according to claim 1, wherein the composition is a cosmetic, or an externally-applied medical or quasi-medical drug.

5. A potentiating method according to claim 1, wherein the component (B) synergistically potentiates the pigmentation alleviating effect of (A) ascorbic acid 2-glucoside.

6. A method for alleviating skin pigmentation according to claim 3, wherein a composition comprising:

(A) ascorbic acid 2-glucoside; and (B) at least one purine nucleic acid-related substance selected from the group adenosine 2'-monophosphate, adenosine 3'-monophosphate, adenosine 5'-monophosphate, and salts thereof, wherein component (B) is 0.1% to 7% (w/w) based on the total amount of the composition;

is applied to the skin.

7. A method for alleviating skin pigmentation according to claim 3, wherein the at least one purine nucleic acid-related substance is adenosine 5'-monophosphate or a salt thereof.

8. A method for alleviating skin pigmentation according to claim 6, wherein the composition is a cosmetic, or an externally-applied medical or quasi-medical drug.

9. A method for alleviating skin pigmentation according to claim 3, wherein the purine nucleic acid-related substance synergistically potentiates the pigmentation alleviating effect of (A) ascorbic acid 2-glucoside.

10. A potentiating method according to claim 1, wherein component (B) is 0.1% to 7% (w/w) based on the total amount of the composition.

* * * * *